United States Patent [19]
Cozzi et al.

[11] Patent Number: 5,246,957
[45] Date of Patent: Sep. 21, 1993

[54] N-IMIDAZOLYL DERIVATIVES OF SUBSTITUTED INDOLE

[75] Inventors: Paolo Cozzi; Antonio Pillan, both of Milan; Maurizio Pulici, Grezzago; Patricia Salvati, Arese; Angelo D. Volpi, Cornaredo, all of Italy

[73] Assignee: Farmitalia Carlo Erba S.r.l., Milan, Italy

[21] Appl. No.: 870,084

[22] Filed: Apr. 17, 1992

[30] Foreign Application Priority Data

Apr. 24, 1991 [GB] United Kingdom ................ 9108811

[51] Int. Cl.$^5$ .................. A61K 31/415; C07D 403/10
[52] U.S. Cl. .................................. 514/397; 548/312.1
[58] Field of Search ..................... 514/397; 548/312.1, 548/336

[56] References Cited

U.S. PATENT DOCUMENTS

| | | | |
|---|---|---|---|
| 4,410,539 | 10/1983 | Cross et al. | 424/273 R |
| 4,496,572 | 1/1985 | Cross et al. | 514/337 |
| 4,767,865 | 8/1988 | Johnson et al. | 546/342 |
| 5,026,722 | 6/1991 | Oxford et al. | 548/336 |
| 5,081,138 | 1/1992 | Gillard et al. | 514/381 |

FOREIGN PATENT DOCUMENTS

| | | |
|---|---|---|
| 0166591 | 1/1986 | European Pat. Off. |
| 0363789 | 4/1990 | European Pat. Off. |
| 455777 | 7/1968 | Switzerland |
| 2225012 | 5/1990 | United Kingdom |

OTHER PUBLICATIONS

Annual Reports in Medical Chemistry, vol. 22, pp. 95–105, 1987, P. E. Cross, et al., "Thromboxane Synthetase Inhibitors and Antagonists".

Annual Reports in Medical Chemistry, vol. 25, pp. 99–108, 1990, E. W. Collington, et al., "Thromoxine Synthase Inhibitors and Receptor Antagonists".

(List continued on next page.)

Primary Examiner—Patricia L. Morris
Attorney, Agent, or Firm—Oblon, Spivak, McClelland, Maier & Neustadt

[57] ABSTRACT

The invention provides N-imidazolyl derivatives of substituted indole of general formula (I)

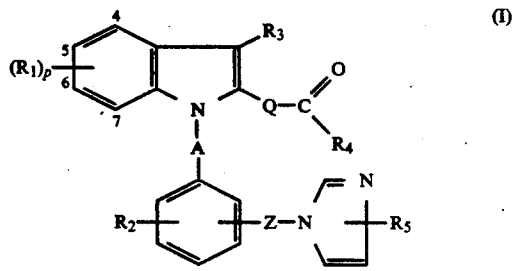

wherein
p is an integer of 1 to 4;
A is a straight or branched $C_1$–$C_4$ alkylene chain;
B is a direct linkage, a straight or branched, unsaturated or saturated $C_1$–$C_4$ hydrocarbon chain;
Q is a straight or branched, saturated or unsaturated $C_1$–$C_9$ hydrocarbon chain, or said chain is interrupted by an oxygen atom;
each of $R_1$ and $R_2$ independently is hydrogen, $C_1$–$C_4$ alkyl, $C_1$–$C_4$ alkoxy, $C_1$–$C_4$ alkylthio, $C_1$–$C_4$ alkylsulfonyl, halogen or trihalomethyl;
each of $R_3$ and $R_5$, independently, is hydrogen or $C_1$–$C_4$ alkyl;
$R_4$ is a —$OR_6$ or —$N(R_6R_7)$ group, wherein each of $R_6$ and $R_7$ independently is hydrogen, $C_1$–$C_4$ alkyl, phenyl or benzyl; or a pharmaceutically acceptable salt thereof, which are useful in the treatment of a disease state in which an enhancement of $TxA_2$ synthesis exerts a pathogenic effect.

5 Claims, No Drawings

OTHER PUBLICATIONS

Derwent Publications, SE-455777, Jul. 15, 1968, 34122F.

Derwent Publications, SE-454858, Jun. 28, 1968, 33372F.

Derwent Publications, EP-080154, Jun. 1, 1983, 54325K.

Derwent Publications, US-4,436,746, Mar. 13, 1984, 84-081725K.

Derwent Publications, US-4,894,386, Jan. 16, 1990, 90-075612.

Derwent Publications, EP-054417, Jun. 23, 1982, 52821E.

Derwent Publications, WO-91-06537, May 16, 1991, 91-164112.

Derwent Publications, EP-242167, Oct. 21, 1987, 87-293543.

Derwent Publications, EP-290145, Nov. 9, 1988, 88-316400.

Derwent Publications, WO-9113060, Sep. 5, 1991, 91-281398.

Derwent Publications, US-5,081,138, Dec. 17, 1986, 88-206771.

Derwent Publications, US-5,081,145, Jan. 14, 1992, 92-048334.

N-IMIDAZOLYL DERIVATIVES OF SUBSTITUTED INDOLE

The present invention relates to new N-imidazolyl derivatives of substituted indole, to a process for their preparation, to pharmaceutical compositions containing them and to their use as therapeutic agents.

The present invention provides novel compounds having the general formula (I)

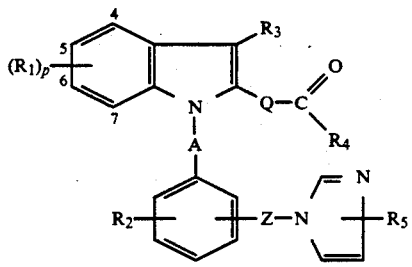

wherein
p is an integer of 1 to 4;
A is a straight or branched $C_1$-$C_4$ alkylene chain;
Z is a direct linkage, a straight or branched, unsaturated or saturated $C_1$-$C_4$ hydrocarbon chain;
Q is a straight or branched, saturated or unsaturated $C_1$-$C_9$ hydrocarbon chain, or said chain is interrupted by an oxygen atom;
each of $R_1$ and $R_2$ independently is hydrogen, $C_1$-$C_4$ alkyl, $C_1$-$C_4$ alkoxy, $C_1$-$C_4$ alkylthio, $C_1$-$C_4$ alkylsulfonyl, halogen or trihalomethyl;
each of $R_3$ and $R_5$, independently, is hydrogen or $C_1$-$C_4$ alkyl;
$R_4$ is a —$OR_6$ or —$N(R_6R_7)$ group, wherein each of $R_6$ and $R_7$ independently is hydrogen, $C_1$-$C_4$ alkyl, phenyl or benzyl; and the pharmaceutically acceptable salts thereof.

The invention also includes within its scope all the possible isomers, steroisomers and their mixtures and the metabolites and the metabolic precursors or bioprecursors of the compounds of formula (I).

When p is higher than 1, then each $R_1$ substituent may be the same or different.

The alkyl, alkoxy, alkylthio and alkylsulfonyl groups may be branched or straight chain groups.

A $C_1$-$C_4$ alkyl group is e.g. methyl, ethyl, propyl, isopropyl, butyl or tert-butyl, preferably methyl or ethyl.

A $C_1$-$C_4$ alkoxy group is e.g. methoxy, ethoxy, propoxy, isopropoxy, butoxy or tert-butoxy, preferably methoxy, ethoxy or propoxy.

A $C_1$-$C_4$ alkylthio group is e.g. methylthio, ethylthio, propylthio or butylthio, preferably methylthio or ethylthio.

A $C_1$-$C_4$ alkylsulfonyl group is preferably methylsulfonyl.

A halogen atom is bromine, chlorine or fluorine, preferably bromine or fluorine.

A straight or branched $C_1$-$C_4$ alkylene chain is e.g. —$CH_2$—, —$CH_2$—$CH_2$—, or —$CH(CH_3)$—$CH_2$— in particular —$CH_2$— or —$CH_2$—$CH_2$—.

A trihalomethyl group is e.g. trichloromethyl or trifluoromethyl, preferably trifluoromethyl.

A straight or branched, saturated or unsaturated $C_1$-$C_4$ hydrocarbon chain is e.g. a chain chosen from —$CH_2$—, —$CH_2$—$CH_2$—, —$CH_2$—$CH_2$—$CH_2$—, —$CH(CH_3)$—$CH_2$— or —$CH$=$CH$—, in particular —$CH_2$— or —$CH_2$—$CH_2$—.

A straight or branched saturated or unsaturated $C_1$-$C_9$ hydrocarbon chain is e.g. —$CH_2$—, —$CH_2$—$CH_2$—, —$CH_2$—$CH_2$—$CH_2$—, —$CH_2$—$CH_2$—$CH_2$—$CH_2$—, —$CH_2$—$CH(CH_3)$—, —$CH(CH_3)$—$CH_2$—, —$CH_2$—$C(CH_3)_2$—, —$CH_2$—$CH(CH_3)$—$CH_2$, —$CH(CH_3)$—$CH(CH_3)$—, —$CH$=$CH$— or —$CH$=$CH$—$CH_2$—.

When said hydrocarbon chain is interrupted by an oxygen atom, the thus obtained chain is preferably —$CH_2$—O—$CH_2$— or —$CH_2$—$CH_2$—O—$CH_2$—.

Pharmaceutically acceptable salts of the compounds of the invention include acid addition salts, with inorganic, e.g. nitric, hydrochloric, hydrobromic, sulphuric, perchloric and phosphoric acids, or organic, e.g. acetic, propionic, glycolic, lactic, oxalic, malonic, malic, maleic, tartaric, citric, benzoic, cinnamic, mandelic and salicylic acids, and salts with inorganic, e.g. alkali metal, especially sodium or potassium, bases or alkaline-earth metal, especially calcium or magnesium, bases, or with organic bases, e.g. alkylamines, preferably triethylamine, or basic naturally occurring aminoacids, preferably arginine.

As stated above the present invention also includes within its scope pharmaceutically acceptable bioprecursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of the invention are the compounds of formula (I), wherein,
p is 1 or 2;
A is —$CH_2$— or —$CH_2$—$CH_2$—;
B is direct linkage or —$CH_2$—;
Q is —$CH_2$—$CH_2$—, —$CH_2$—$CH_2$—$CH_2$—, $CH_2$—$C(CH_3)_2$—, —$CH_2$—$CH_2$—$C(CH_3)_2$—, —$CH_2$—O—$CH_2$—, —$CH_2$—$CH_2$—O—$CH_2$—;
each of $R_1$, $R_2$, independently is hydrogen, $C_1$-$C_4$ alkyl, halogen or trifluoromethyl;
$R_3$ is $C_1$-$C_4$ alkyl;
$R_5$ is hydrogen;
$R_4$ is —$OR_6$ or —$NHR_6$ wherein $R_6$ is hydrogen or $C_1$-$C_4$ alkyl and the pharmaceutically acceptable salts thereof.

More preferred compounds of the invention are compounds of formula (I) wherein:
p is 1 or 2;
A is —$CH_2$—;
Z is a direct linkage or —$CH_2$—;
Q is —$CH_2$—$CH_2$—, —$CH_2$—$CH_2$—$CH_2$—, —$CH_2$—$C(CH_3)_2$—; —$CH$=$CH$— or —$CH_2$—O—$CH_2$—;
$R_2$ and $R_5$ are hydrogen;
$R_3$ is $C_1$-$C_4$ alkyl;
$R_1$ is halogen or trifluoromethyl;
$R_4$ is $OR_6$ or $NHR_6$ wherein $R_6$ is hydrogen or $C_1$-$C_4$ alkyl; and
the pharmaceutically acceptable salt thereof.

Examples of preferred compounds of formula (I) are the following:
1) 5-Fluoro-1-[[4-(1H-imidazol-1-yl)phenyl]methyl]-3-methyl-1H-indole-2-propanoic acid;
2) 5,7-Difluoro-1-[[4-(1H-imidazol-1-yl)phenyl]methyl]-3-methyl-1H-indole-2-propanoic acid;

3) 5-Fluoro-1-[[3-(1H-imidazol-1-yl)phenyl]methyl]-3-methyl-1H-indole-2-propanoic acid;
4) 5-Fluoro-1-[[4-(1H-imidazol-1-ylmethyl)phenyl]methyl]-3-methyl-1H-indole-2-propanoic acid;
5) Ethyl 5-fluoro-1-[[4-(1H-imidazol-1-yl)phenyl]methyl]-3-methyl-1H-indole-2-propanoate;
6) 5-Fluoro-1-[[4-(1H-imidazol-1-yl)phenyl]methyl]-3-methyl-1H-indole-2-propanamide;
7) 5-Fluoro-1-[[4-(1H-imidazol-1-yl)phenyl]methyl]-$\alpha,\alpha$,3-trimethyl-1H-indole-2-propanoic acid;
8) 5,7-Difluoro-1-[[4-(1H-imidazol-1-yl)phenyl]methyl]-$\alpha,\alpha$,3-trimethyl-1H-indole-2-propanoic acid;
9) 5-Fluoro-1-[[4-(1H-imidazol-1-yl)phenyl]methyl]-3-methyl-1H-indole-2-butanoic acid;
10) Ethyl 5-fluoro-1-[[4-(1H-imidazol-1-yl)phenyl]methyl]-3-methyl-1H-indole-2-butanoate;
11) 5-Fluoro-1-[[4-(1H-imidazol-1-yl)phenyl]methyl]-$\alpha,\alpha$,3-trimethyl-1H-indole-2-butanoic acid;
12) 5,7-Difluoro-1-[[4-(1H-imidazol-1-yl)phenyl]methyl]-$\alpha,\alpha$,3-trimethyl-1H-indole-2-butanoic acid;
and pharmaceutically acceptable salts thereof.

The structural formulae of the above numbered compounds, indicated according to their progressive number, are reported in the following table.

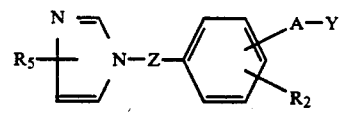

wherein A, Z, $R_2$ and $R_5$ are as defined above and Y is a leaving group; or b) reacting a compound of formula (IV)

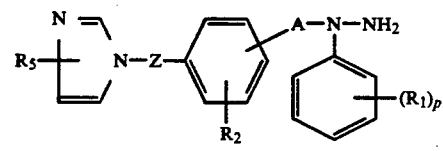

wherein p, A, Z, $R_1$, $R_2$ and $R_5$ are as defined above, with a compound of formula (V)

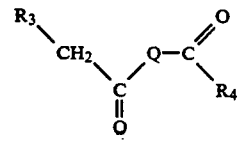

wherein Q, $R_3$ and $R_4$ are as defined above; or c) reacting a compound of formula (VI) or a salt thereof

| COMPOUND | A | Z | POSITION OF B ON PHENYL | $R_1$ | $R_2$ | $R_3$ | $R_4$ | $R_5$ | Q |
|---|---|---|---|---|---|---|---|---|---|
| 1 | $CH_2$ | BOND | PARA | 5F | H | $CH_3$ | OH | H | $-CH_2-CH_2-$ |
| 2 | $CH_2$ | BOND | PARA | 5F, 7F | H | $CH_3$ | OH | H | $-CH_2-CH_2-$ |
| 3 | $CH_2$ | BOND | META | 5F | H | $CH_3$ | OH | H | $-CH_2-CH_2-$ |
| 4 | $CH_2$ | $CH_2$ | PARA | 5F | H | $CH_3$ | OH | H | $-CH_2-CH_2-$ |
| 5 | $CH_2$ | BOND | PARA | 5F | H | $CH_3$ | OET | H | $-CH_2-CH_2-$ |
| 6 | $CH_2$ | BOND | PARA | 5F | H | $CH_3$ | $NH_2$ | H | $-CH_2-CH_2-$ |
| 7 | $CH_2$ | BOND | PARA | 5F | H | $CH_3$ | OH | H | $-CH_2-C(CH_3)_2-$ |
| 8 | $CH_2$ | BOND | PARA | 5F, 7F | H | $CH_3$ | OH | H | $-CH_2-C(CH_3)_2-$ |
| 9 | $CH_2$ | BOND | PARA | 5F | H | $CH_3$ | OH | H | $-CH_2-CH_2-CH_2-$ |
| 10 | $CH_2$ | BOND | PARA | 5F | H | $CH_3$ | OH | H | $-CH_2-CH_2-CH_2-$ |
| 11 | $CH_2$ | BOND | PARA | 5F | H | $CH_3$ | OH | H | $-CH_2-CH_2-C(CH_3)_2-$ |
| 12 | $CH_2$ | BOND | PARA | 5F, 7F | H | $CH_3$ | OH | H | $-CH_2-CH_2-C(CH_3)_2-$ |

The compounds of the invention and the salts thereof can be obtained by a process comprising:

a) reacting a compound of formula (II) or a salt thereof

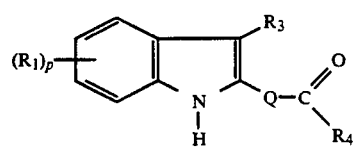

wherein p, Q, $R_1$, $R_3$ and $R_4$ are as defined above, with a compound of formula (III)

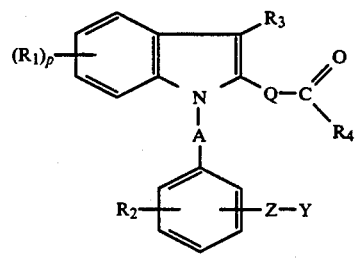

where p, A, Z, Q, $R_1$, $R_2$, $R_3$, $R_4$ are as defined above and Y is a leaving group, with imidazole, a $C_1$-$C_4$ alkylimidazole or a salt thereof, and if desired, converting a compound of formula (I) into another compound of formula (I), and/or, if desired converting a compound of formula (I) into a salt thereof, and/or, if desired, converting a salt of a compound of formula (I) into a free compound, and/or, if desired, separating a mixture of isomers of a compound of formula (I) into the single isomers.

A leaving group Y in a compound of formula (III) or of formula (VI) is preferably a halogen, e.g. bromine or clorine, or a mesyl or a tosyl group.

The reaction of a compound of formula (II), or a salt thereof with a compound of formula (III) can be is carried out using a strong base such as sodium hydroxide, potassium t-butoxide, potassium hydride, ethyl magnesium bromide or potassium hexamethyl-disilazide in presence of a suitable organic solvent such as dimethylformamide, dimethylacetamide, tetrahydrofurane, toluene, ethyl acetate, benzene, or a mixture thereof, at a temperature ranging from about −20° C. to about 50° C.

The reaction of a compound of formula (IV) with a compound of formula (V) can be carried out using the standard condition of the Fisher indolic synthesis (a well known reaction described, for example, in "Heterocyclic Compound", 25, parts I, II and III, W. J. Houlihan, ed, Interscience, John Wiley & Sons, New York, 1979) e.g. by operating at reflux temperature in an organic solvent, e.g. an alkanol, in particular methanol, ethanol, isopropylic alcohol, benzene or toluene. The reaction may be performed in presence of a acid catalyst, e.g. a strong mineral acid, in particular sulphuric acid or hydrochloric acid.

The reaction of compound of formula (VI), or a salt thereof, with imidazole or $C_1$-$C_4$ alkylimidazole can be carried out in the presence of a base such as triethylamine or preferably using an excess of imidazole or alkylimidazole.

When a compound of formula (VI) or a salt thereof is reacted with a salt of imidazole or of a $C_1$-$C_4$ alkylimidazole, the salt of the latter compound is e.g. a potassium or sodium salt and the reaction does not require the presence of any additional basic agent.

The reaction is performed in the presence of a suitable organic solvent such as ethanol, methanol, dimethylformamide, dimethylacetamide, or in absence of any solvent, e.g. in fusion with an excess of imidazole or $C_1$-$C_4$ alkylimidazole, at a temperature ranging from about 70° C. to about 170°. When in a compound of formula (VI) B is a direct linkage the reaction can be performed in radicalic conditions using catalyst such as $Cu_2Br_2$ or Cu powder.

A compound of formula (I) may be converted, if desired, into another compound of formula (I).

These optional conversions may be carried out by methods known in themselves.

A compound of formula (I) containing an esterified carboxy group, may be converted into a compound of formula (I) containing a free carboxy group, by acidic or alkaline hydrolysis, operating at temperatures ranging from the room temperature to about 100° C.

A compound of formula (I) containing a free carboxy group, may be converted into a compound of formula (I) containing an esterified carboxy group by esterification, e.g. via the corresponding acid halide, e.g. chloride, reacting with an excess of a suitable $C_1$-$C_4$ alkyl alcohol, or by direct esterification by means of acidic catalysis in the presence of dry HCl, $SOCl_2$ or $BF_3$-etherate.

A compound of formula (I) containing a free or esterified carboxy group may be converted into a compound of formula (I) containing a $-CONR_6R_7$ group, wherein $R_6$ and $R_7$ are as defined above. Accordingly, the conversion of an esterified carboxy group into the corresponding amide may be performed by direct reaction with ammonia or an appropriate amine in a suitable aprotic solvent, e.g., ether or benzene, or using an excess of the amine as solvent, at temperature ranging from room temperature to reflux.

The conversion of free carboxy group into a corresponding amide may be carried out via an intermediate reactive derivative which may be isolated or not.

Intermediate reactive derivatives may be active esters e.g. $NO_2$-phenyl esters, or N-hydroxysuccinimide esters, acid halides, preferably chloride, mixed anhydrides, e.g. ethoxycarbonyl or tert-butylcarbonyl anhydrides, or reactive intermediates obtained in situ by reaction of the acid with dicyclohexylcarbodiimide or carbonyldiimidazole. The reactive intermediates obtained following conventional ways, as those usually employed in the synthesis of peptides, are reacted with ammonia or an appropriate amine in a suitable solvent or with an excess of the amine itself at temperatures ranging from about −10° C. to about 50° C.

The optional salification of a compound of formula (I) as well as the conversion of a salt into a free compound and the separation of a mixture of isomers into the single isomers may be carried out by conventional methods.

For example the separation of a mixture of geometric isomers, e.g. cis- and trans- isomers, may be carried out by fractional crystallization from a suitable solvent or by chromatography, either column chromatography or high pressure liquid chromatography.

A compound of formula (II) may be obtained by reacting a compound of formula (VII)

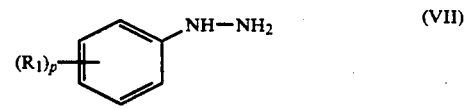

wherein $R_1$ and p are as defined above, with a compound of formula (V) as defined above using the standard condition of Fisher indolic synthesis as described above.

A compound of formula (III) can be obtained by reacting a compound of formula (VIII)

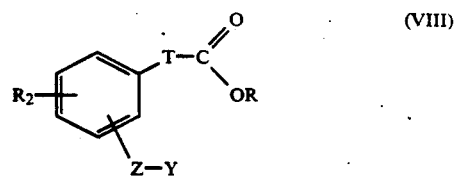

wherein Z and Y are as defined above, T is a direct linkage or a straight or branched $C_1$-$C_3$ alkylene chain and R is a lower, e.g. $C_1$-$C_4$ alkyl group, with imidazole, $C_1$-$C_4$ alkylimidazole or a salt thereof.

The reaction can be carried out in the presence of a base such as triethylamine, or preferably using an excess of imidazole or $C_1$-$C_2$ alkylimidazole in a suitable organic solvent such as ethanol, methanol, dimethylformamide, dimethylacetamide, or in absence of any solvent, e.g. in fusion with excess of imidazole or $C_1$-$C_2$ alkylimidazole, at temperatures ranging from about 70° C. to about 165° C.

If required a catalyst, e.g. CuBr or Cu can additionally be used in the above said reaction.

The imidazole ring containing ester so obtained can, by usual and well known methods, be transformed in a compound of formula (III), e.g. by reducing with $LiAlH_4$ and halogenating the so obtained alcohols with $SOCl_2$, $SOBr_2$ or $PCl_5$.

Alternatively a compound of formula (III) wherein B is a direct linkage and A is —$CH_2$— can be obtained by reacting a compound of formula (IX)

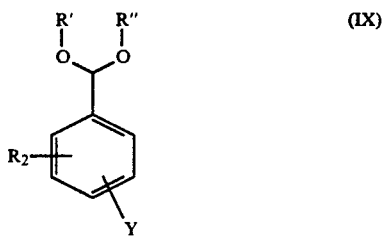

wherein $R_2$ and Y are as defined above, and wherein R' and R" are $C_1$-$C_6$ alkyl groups or taken together form a 1,3-dioxolane or a 1,3 dioxane ring, with imidazole, $C_1$-$C_4$ alkylimidazole or preferably with their sodium or potassium salts, in presence of a catalyst e.g. $Cu_2Br_2$ or Cu powder, using a suitable organic solvent such as dimethylformamide, dimethylacetamide or dimethoxyethane at temperatures ranging from about 100° to about 200° C. The substituted benzaldehyde ketal so obtained can be transformed in a compound of formula (III) following well known methods e.g. hydrolysis of the acetal group in acid condition, reduction of aldehyde with $NaBH_4$ or $LiAlH_4$ and halogenation with $SOCl_2$ or $SOBr_2$. The compounds of formula (IV) are obtainable by following the known methods of N alkylation of phenylhydrazines using compounds of formula (III) as alkylating agents.

A compound of formula VI may be obtained reacting a compound of formula (II) with a compound of formula (X)

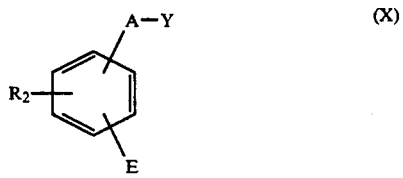

wherein E is either Y, as defined above, or a chemical precursor of a group Z—Y, wherein Z and Y are as defined above, thus obtaining, respectively, a compound of formula (VI) wherein Z is a direct linkage or, after converting the chemical precursor in a Z—Y group by the well known methods in the art, a compound of formula (VI) wherein B is a $C_1$-$C_4$ hydrocarbon chain.

A chemical precursor of a group Z—Y may be for instance a ketal or ester group well known in the art.

The compounds of formula (V), (VII), (VIII), (IX) and (X) are known compounds or may be obtained by procedures well known in organic chemistry.

When in the intermediate compounds, according to the present invention, groups are present which may interfere with the reactions herein described, these groups can be protected before the reaction takes place and then deprotected at the end of the reaction according to known methods, e.g. those used in the chemistry of peptides.

PHARMACOLOGY

Thromboxane ($TxA_2$) is a derivative of arachidonic acid metabolism that aggregates platelets and amplifies their response to a variety of other aggregating agents.

In addition $TxA_2$ contracts vascular, bronchial and tracheal smooth muscle cells and glomerular mesangial cells.

Therefore $TxA_2$ is involved in a variety of pathologies such as: cardiovascular diseases (myocardial infraction and angina), cerebrovascular diseases (stroke, transient ischemic attack and migraine), peripheral vascular diseases (microangiopathies), renal diseases (glomerulosclerosis, lupus nephritis, diabetic nephropathy), and respiratory diseases (bronchoconstriction and asthma) and more in general is involved in atherosclerosis.

$TxA_2$ exerts its action in platelet and smooth muscle cells through the occupancy of receptor(s), the $TxA_2$ receptor(s). The effects of $TxA_2$ can be counteracted by an agent possessing $TxA_2$ receptors antagonistic properties and/or by an agent inhibiting the enzymes involved in the synthesis of $TxA_2$, in particular $TxA_2$-synthase which catalyzes the formation of $TxA_2$ from cyclic endoperoxides prostaglandin $G_2$ and prostaglandin $H_2$ without affecting the synthesis of other prostaglandins.

Agents which inhibit $TxA_2$ action either by antagonizing $TxA_2$ and/or inhibiting $TxA_2$-synthase may be expected to be of therapeutic value in the treatment of the above-mentioned diseases and in other pathological conditions in which $TxA_2$ is involved.

The compounds of the present invention, which possess these activities, are believed to be effective in the treatment of a disease state in which an enhancement of $TxA_2$ synthesis exerts a pathogenic effect, for instance those mentioned above.

METHODS

The effects of a representative group of compounds of the invention were evaluated, in comparison with known compounds, on $TxB_2$ synthesis inhibition in vitro, in whole blood of normal rats, and on $TxA_2$ antagonism in a binding assay in washed human platelets.

$TxB_2$ Synthesis Inhibition

Blood was withdrawn from the abdominal aorta of normal Sprague Dawley rats (Charles River Italy) under light ether anaestesia. The blood was immediately divided in portions of 0.5 ml and distributed in glass tubes each containing a concentration of the test compound, or of the reference compounds.

Samples were then allowed to clot for 1 hour at 37° C., centrifuged at 3000 rpm for 10 min, and serum collected and stored at −20° C. until assayed. $TxB_2$ levels were determined by RIA according to previously described procedures (Thromb. Res. 17, 3/4, 317, 1980) using highly sensitive antibody.

Displacement of [³H]-SQ 29,548 Binding to Washed Human Platelets

Blood from healthy volunteers of both sexes who had not taken any medication for at least 10 days was collected into one-tenth volume of acid citrate dextrose containing indomethacin (28 μM). Platelet rich plasma (PRP), obtained by centrifugation of the blood at 200× g for 20 min, was washed twice (1000× g for 10 min). The platelets were then resuspended in Tyrode-Hepes buffer (pH 7.4) to a final concentration of $5-10 \times 10^{-8}$ cells/ml and incubated for 0–60 min at 25° with [³H]-SQ 29,548 (5 nM). For displacement experiments various concentrations ($10^{-9}-10^{-4}$M) of competing ligands were added and incubated for 30 min at 25° C. Non-specific binding was determined in the presence of 50 μM U46619 and was approximately 5% of total binding of [³H]-SQ 29,548. After the incubation, 4 ml of ice-cold TRIS-HCl buffer (10 mM, pH 7.4) was added to each tube and the reaction mixture was immediately filtered by suction through a Whatman GF/C glass filter disc which was washed 2 times with ice-cold TRIS-HCl (4 ml) and counted for radioactivity by a Packard β-counter.

The binding data were analysed by computerized non-linear curve fitting using the Ligand program and expressed as IC$_{50}$.

In Table 1, as an example, the results obtained in the binding test (washed human platelets) with the representative compounds of the invention, having internal codes FCE 27005 and FCE 27093, are compared to those obtained with the reference standard compounds, BM 13505 and BM 13177 (Naunyn-Schmideberg's Arch. Pharmacol. 1986, 332 (Suppl.) Abst. 144 S.R. 36; Cardiovasc. Drug Rev. 1988, 6:20–34).

These results show that the compounds FCE 27005 and FCE 27093 have an affinity for the receptor greater than those of compounds BM 13505 and BM 13177.

TABLE 1

| | ³H SQ 29548 binding displacement (washed human platelet) IC$_{50}$ (M) (n = 3) |
|---|---|
| BM 13505 | $1.2 \times 10^{-7}$ |
| BM 13177 | $7.3 \times 10^{-6}$ |
| FCE 27005 | $3.29 \times 10^{-8}$ |
| FCE 27093 | $1.19 \times 10^{-8}$ |

In table 2, as an example, the results obtained on TxB$_2$ synthesis in normal rats, with the compound of the invention having internal code FCE 27093, on TxB$_2$ synthesis in normal rats, are compared with those obtained with the reference standard dazoxiben and ASA; limits when calculated are reported in brackets.

TABLE 2

In vitro effect on TxB$_2$ synthesis in normal rats.
Data are expressed as IC$_{50}$ (M) and limits for p = 0.95

| Compound | IC$_{50}$ (M) (whole blood) | LIMITS |
|---|---|---|
| FCE 27093 | $1.19 \times 10^{-6}$ | $(0.59-3.66 \times 10^{-6})$ |
| Dazoxiben | $1.2 \times 10^{-6}$ | $(0.7-1.9 \times 10^{-6})$ |
| ASA | $3.1 \times 10^{-5}$ | $(2.6-3.8 \times 10^{-5})$ |

In the above Table 1 and 2 internal code FCE 27005 means 5-Fluoro-1-[[4-(1H-imidazol-1-yl)phenyl]methyl]-3-methyl-1H-indole-2-propanoic acid, internal code FCE 27093 means 5-Fluoro-1-[[4-(1H-imidazol-1-yl)phenyl]methyl]-3-methyl-1H-indole-2-butanoic acid and ASA means acetylsalicilic acid. As the compounds of the present invention are both TxA$_2$ synthase inhibitors and PGH$_2$/TxA$_2$ antagonists in the platelets, on the basis of the state of the art, as reported e.g. in J. Clin. Invest. 80, 1435 (1987) and in Adv. Prostaglandins, Thromboxanes, Leukotrienes Res. Vol. 17 (1987) p. 49, these compounds are particularly suitable for the treatment of a disease state in which an enhancement of TxA$_2$ synthesis exerts a pathogenic effect, for instance in those mentioned above.

In particular in the treatment of renal failure the compounds of the invention may be used in association with an angiotensin converting enzyme inhibitor (ACEI), both as separated and substantially concomitant administration. The compounds of the invention can also be used to prevent or treat cyclosporin A-induced nephrosis in mammals.

The compounds of the invention can also be used in association with thrombolytic agents (e.g. tPA, Streptokinase, pro-Urokinase) in order to reduce the dose of the latter required in thrombolytic therapy, and to lower the incidence of reocclusion and possibly hemorrhage.

A further application of the compounds of the invention is the prevention and/or treatment of restenosis after percutaneous transluminal angioplasty.

The toxicity of the compounds of the invention is negligible, therefore they can be safely used in therapy. Mice and rats which had been deprived of food for nine hours were treated orally with single administrations of increasing doses of compounds of the invention, then housed and normally fed.

The orientative acute toxicity (LD$_{50}$) was assessed on the seventh day after the treatment.

In view of their high activity the compounds of the invention can be safely used in medicine. The therapeutic regimen for the different clinical syndromes must be adapted to the type of pathology, taking into account, as usual, also the route of administration, the form in which the compound is administered and the age, weight and conditions of the subject involved. The oral route is employed, in general, for all conditions requiring such compounds. Preference is given to intravenous injection or infusion for the treatment of acute pathological states.

For maintenance regimens the oral or parental, e.g. intramuscular, route is preferred.

The dosage level suitable for oral administration to adult humans of the compounds of the invention, e.g. 5-Fluoro-[[4-(1H-imidazol-1-yl)phenyl]methyl]-3-methyl-1H-indole-2-propanoic acid, may range from about 50 mg to about 500 mg per dose 1 to 3 times a day.

Of course, these dosage regimens may be adjusted to provide the optimal therapeutic response.

The nature of the pharmaceutical compositions containing the compounds of this invention in association with pharmaceutically acceptable carriers or diluents will be dependent upon the desired route of administration. The composition may be formulated in the conventional manner with the usual ingredients. For example, the compounds of the invention may be administered in the form of aqueous or oily solutions, or suspensions, tablets, pills, gelatine capsules, syrups, drops or suppositories.

Thus, for oral administration, the pharmaceutical composition containing the compounds of this invention are preferably tablets, pills or gelatine capsules which contain the active substance together with diluents, such as lactose, dextrose, sucrose, mannitol, sorbitol, cellulose; lubricants, for instance silica, talc, stearic acid, magnesium or calcium stearate, and/or polyethylene glycols; or they may also contain binders, such as starches, gelatine, methylcellulose, carboxymethylcellulose, gum-arabic, tragacanth, polyvinylpyrrolidone; disaggregating agents, such as starches, alginic acid, alginates, sodium starch glycolate; effervescing mixtures; dyestuffs; sweeteners; wetting agents, such as lecithin, polysorbates, laurylsulphates; and in general, non-toxic and pharmacologically inactive substances used in pharmaceutical formulations. Said pharmaceutical preparations may be manufactured in known manner, for example by means of mixing, granulating, tabletting, sugar-coating, or film-coating processes. The liquid dispersions for oral administration may be e.g. syrups, emulsions and suspensions.

The syrups may contain as carrier, for example, saccharose or saccharose with glycerine and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain together with the active compound a pharmaceutically acceptable carrier, e.g. sterile water, olive oil, ethyl oleate, glycols, e.g. propylene glycol, and if desired, a suitable amount of lidocaine hydrochloride.

The solutions for intravenous injection or infusion may contain as carrier, for example, sterile water or preferably they may be in the form of sterile aqueous isotonic saline solutions.

The suppositories may contain together with the active compound a pharmaceutically acceptable carrier e.g. cocoa-butter, polyethylene glycol, a polyoxyethylene sorbitan fatty acid ester surfactant or lecithin.

The following examples illustrate but do not limit the present invention.

EXAMPLE I

5-Fluoro-1-[[4-(1H-imidazol-1-yl)phenyl]methyl]-3-methyl-1H-indole-2-propanoic acid.

A solution of 198 mg of 5-fluoro-3-methyl-1H-indole-2-propanoic acid in 20 ml of dry DMF is cooled at 0° C., and treated with 155 mg of 55% NaH. The reaction mixture is stirred for 60 minutes at 0° C., then 307 mg of 1-[4-(chloro-methyl)phenyl]-1H-imidazole hydrochloride are added portionwise under nitrogen at 0° C. After stirring at room temperature for 16 hours the mixture is poured into water and washed with methylene chloride. The aqueous solution is neutralized with diluted HCl and extracted with methylene chloride. The organic layer is dried over sodium sulfate and evaporated to dryness. The residue, taken up with acetone, filtered and dried, yields 35 mg of the title compound (m.p. 222° C.)

N.M.R (DMSO-d6) p.p.m: 2.20(3H,s,CH$_3$), 2.37(2H,m,CH$_2$—COOH), 2.95(2H,m,CH$_2$—CH$_2$—COOH), 5.47(2H,s,NCH$_2$), 6.80-7.65(9H, m, benzene H and N—CH=CH—N), 8.16 (1H,s N=CH—N).

Analogously the following compounds can be prepared:

5-Fluoro-1-[[4-(1H-imidazol-1-ylmethyl)phenyl]methyl]-3-methyl-1H-indole-2-propanoic acid, m.p. 192° C.

N.M.R (DMSO-d6) p.p.m: 2.17(3H,s,CH$_3$), 2.33(2H,m,CH$_2$—COOH), 2.90(2H,m,CH$_2$—CH$_2$—COOH), 5.10(2H,s,CH$_2$—imidazole), 5.39(2H,s,NCH$_2$), 6.75-7.30(9H, m, benzene H and N—CH=CH—N), 7.68 (1H,s N=CH—N).

5-Fluoro-1-[[4-(1H-imidazol-1-yl)phenyl]methyl]-3-methyl-1H-indole-2-butanoic acid, m.p. 192°-193° C.

N.M.R (DMSO-d6) p.p.m: 1.7 (2H,m,CH$_2$—CH$_2$—COOH), 2.20 (3H,s,CH$_3$), 2.25 (2H,m,CH$_2$—COOH), 2.25 (2H,m,CH$_2$COOH), 2.74 (2H,m,CH$_2$—CH$_2$—CH2—COOH), 5.45 (2H,s,NCH$_2$), 6.70-7.7 (9H, m, benzene H and N—CH=CH—N), 8.11 (1H,s N=CH—N).

5,7-Difluoro-1-[[4-(1H-imidazol-1-yl)phenyl]methyl]-3-methyl-1H-indole-2-propanoic acid;

5-Fluoro-1-[[3-(1H-imidazol-1-yl)phenyl]methyl]-3-methyl-1H-indole-2-propanoic acid;

5-Bromo-1-[[4-(1H-imidazol-1-yl)phenyl]methyl]-3-methyl-1H-indole-2-propanoic acid;

5-Fluoro-1-[[4-(1H-imidazol-1-yl)phenyl]methyl]-α,α,3-trimethyl-1H-indole-2-propanoic acid;

5-Bromo-1-[[4-(1H-imidazol-1-yl)phenyl]methyl]-α,α,3-trimethyl-1H-indole-2-propanoic acid;

5,7-Difluoro-1-[[(4-(1H-imidazol-1-yl)phenyl]methyl]-α,α,3-trimethyl-1H-indole-2-propanoic acid;

5-Fluoro-1-[[4-(1H-imidazol-1-yl)phenyl]methyl]-α,α,3-trimethyl-1H-indole-2-butanoic acid 5-Chloro-1-[[4-(1H-imidazol-1-yl)phenyl]methyl]-α,α,3-trimethyl-1H-indole-2-butanoic acid and 5,7-Difluoro-1-[[4-(1H-imidazol-1-yl)phenyl]methyl]-α,α,3-trimethyl-1H-indole-2-butanoic acid.

The 5-fluoro-3-methyl-1H-indole-2-propanoic acid used above can be prepared as follows:

A mixture of isopropyl 5-fluoro-3-methyl-1H-indole-2-propanoate (0.42 g),1N sodiumhydroxide (6.3 ml) and methanol (20 ml) are stirred at room temperature for 4 hours. The reaction mixture is poured into water, washed with methylene chloride, acidified with 1N HCl and extracted with methylene chloride. The organic layer, dried and evaporated, affords 0.36 g of 5-fluoro-3-methyl-1H-indole-2-propanoic acid.

The isopropyl 5-fluoro-3-methyl-1H-indole-2-propanoate used above can be prepared as follows:

A mixture of 1-(4-fluorophenyl)hydrazine hydrochloride (1.03 g), ethyl 4-oxo-hexanoate (1.0 g), 2-propanol (25 ml) and H$_2$SO$_4$ is refluxed under nitrogen for 9 hours. After cooling the mixture is poured into a aqueous solution of NaHCO$_3$, extracted with AcOEt and evaporated to dryness to yield 1.45 g of isopropyl 5-fluoro-3-methyl-1H-indole-2-propanoate.

The 1-[4-(chloromethyl)phenyl]-1H-imidazole hydrochloride used above can be prepared as follow:

To a solution of 4-(1-imidazolyl)benzaldehyde (2.5 g) in methanol (20 ml), 1.5 g of NaBH$_4$ are added.

After stirring at room temperature for 3 hours the mixture is poured into water and extracted with methylene chloride. The organic phase is dried and evaporated to dryness to yield 2.0 g of 4-(1-imidazolyl)-benzylalchohol. Alternatively the 4-(1-imidazolyl)-benzylalcohol can be obtained by reduction of the ethyl 4-(1-imidazolyl)-benzoate with LiAlH$_4$.

The 4-(1-imidazolyl)-benzylalcohol thus obtained is solved in diethyl ether and transformed into the corresponding hydrochloride by bubbling gaseous HCl. Filtration yields 2.4 g of the salt which is suspended in 30 ml of benzene and treated with 0.8 ml of SOCl₂ and refluxed for 3 hours. The mixture is evaporated to dryness, taken up with ethyl ether and filtered to give 2.6 g of 1-[4-(chloromethyl)phenyl]-1H-imidazole hydrochloride. m.p. 176°–178° C.

The 4-(1-imidazolyl)benzaldehyde used above can be prepared as follow: 7.36 g of p-bromobenzaldehyde are treated at reflux with ethylene glycol in benzene to obtain the corresponding acetal. 8.51 g of this acetale are added to a solution of 5.12 g of imidazole sodium salt in 100 ml of DMF then 3.63 g of Cu powder are added and the mixture is refluxed for 6 hours, then cooled and poured into diluted chloridic acid and crushed ice. The mixture is warmed at 50° C. for 1 hour, cooled, washed with methylene chloride, neutralized with NaHCO₃, extracted with methylene chloride, dried and evaporated to dryness to give 2.5 g 4-(1-imidazolyl) benzaldehyde.

The ethyl-4-(1-imidazolyl)-benzoate is obtained in good yield reacting the ethyl 4-bromobenzoate with imidazole in radicalic condition using CuBr as catalyst.

EXAMPLE 2

Ethyl 5-fluoro-1-[[4-(1H-imidazol-1-yl)phenyl]methyl]-3-methyl-1H-indole-2-propanoate To a solution of hydrogen chloride in absolute ethanol (50 ml) 5-fluoro-1-[[4-(1H-imidazol-1-yl)phenyl]methyl]-3-methyl-1H-indole-2-propanoic acid (0.5 g) is added. The reaction mixture is heated at 60° C. for 3 hours and then evaporated under reduced pressure to dryness. The residue, taken up with ethylether and filtered, yields 0.45 g of the title compound.

Analogously, the following compound can be prepared:
ethyl 5-fluoro-1-[[4-(1H-imidazol-1-yl)phenyl]methyl]-3-methyl-1H-indole-2-butanoate.

EXAMPLE 3

5-Fluoro-1-[[4-(1H-imidazol-1-yl)phenyl]methyl]-3-methyl-1H-indole-2-propanamide A suspension of 5-fluoro-1-[[4-(1H-imidazol-1-yl)phenyl]methyl]-3-methyl-1H-indole-2-propanoic acid (1.0 g) in DMF (10 ml) is treated with SOCl₂ (0.5 g) and, after cooling a gaseous NH₃ is passed through the reaction mixture for 6 hours. The ammonium salt is filtered off and ether is added to the solution. The so obtained precipitated is filtered and dried to give 0.8 g of the title compound.

EXAMPLE 4

5-Fluoro-1-[[4-(1H-imidazol-1-yl)phenyl]methyl]-3-methyl-1H-indole-2-propanoic acid.

A mixture of 1-[(4-1H-imidazol-1-yl)benzyl]-1-(4-fluorophenyl)hydrazine hydrochloride (1.7 g), ethyl 4-oxo-hexanoate (0.85 g) and 2-propanol (100 ml) is refluxed under nitrogen for 9 hours. After cooling the reaction mixture is evaporated to dryness. The resulting residue is purified through a silica gel column eluting with methylene chloride/methanol (95/5) to give 0.7 g of a mixture of ethyl 5-fluoro-2-[[4-(1H-imidazol-1-yl)phenyl]methyl]-3-methyl-1H-indole-2-propanoate and isopropyl 5-fluoro-1-[[4-(1H-imidazol-1-yl)phenyl]methyl]-3-methyl-1H-indole-2-propanoate.

The mixture of ethyl and isopropyl esters is added of methanol (30 ml), water (30 ml) and potassium hydroxide (0.5 g). The resulting mixture is refluxed for 6 hours.

After cooling the methanol is evaporated under reduced pressure and the resulting aqueous solution is neutralized with HCl solution and acidified with acetic acid.

The resulting solid is filtered, washed with water and dried to yield 0.4 g of the title compound, m.p. 222° C. The 1-[(4-1H-imidazol-1-yl)benzyl]-1-(4-fluorophenyl)-hydrazine hydrochloride used above is prepared as follows: a mixture of 1-(4-fluorophenyl)hydrazine hydrochloride (3.3 g), 1-[4-(chloromethyl)phenyl]-1H-imidazole hydrochloride (3.1 g), triethylamine (6.6 ml) and toluene (200 ml) is refluxed under nitrogen for 13 hours. After cooling the mixture is filtered and the solution is evaporated to dryness. The residue is purified through a silica gel column eluting with methylene chloride/methanol (100/5) to give 2.0 g of 1-[(4-1H-imidazol-1-yl)benzyl]-1-(4-fluorophenyl)hydrazine hydrochloride, ms: m/e 282 (M+), 158,157.

EXAMPLE 5

Tablets, each weighing 150 mg and containing 50 mg of the active substance can be manufactured as follows: Composition (for 10,000 tablets) 5-Fluorol-[[4-(1H-imidazol-1-yl)phenyl]methyl]-3-methyl-1H-indole-2-propanoic acid

| Lactose | 710 g |
|---|---|
| Corn starch | 237.5 g |
| Talc powder | 37.5 g |
| Magnesium stearate | 15 g |

5-Fluoro-1-[[4-(1H-imidazol-1-yl)phenyl]methyl]-3-methyl-1H-indole-2-propanoic acid, lactose and a half of the corn starch are mixed; the mixture is then forced through a sieve of 0.5 mm openings. Corn starch (18 mg) is suspended in warm water (180 ml). The resulting paste is used to granulate the powder. The gramules are dried, comminuted on a sieve of sieve size 1.4 mm, then the remaining quantity of starch, talc and magnesium stearate are added, carefully mixed, and processed into tablets using punches of 8 mm diameter.

We claim:

1. A compound of formula (I)

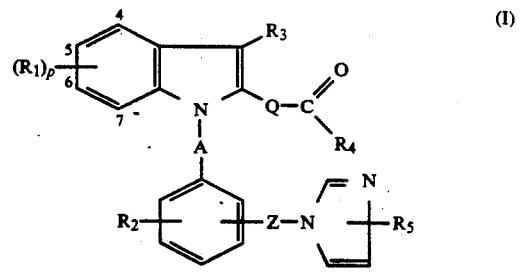

wherein
p is an integer of 1 to 4;
A is a straight or branched $C_1$–$C_4$ alkylene chain;
Z is a direct linkage or a member selected from the group consisting of —CH₂—, —CH₂—CH₂—, —CH₂—CH₂—CH₂—, —CH(CH₃)—CH₂— and —CH=CH—;
Q is a member selected from the group consisting of —CH₂—, —CH₂—CH₂—, —CH₂—CH₂—CH₂—, —CH₂—CH₂—CH₂—CH₂—, —CH₂—CH(CH₃)—, —CH(CH₃)—CH₂—, —CH₂—C(CH₃)₂—, —CH₂—CH(CH₃)—CH₂—, —CH(CH₃)—CH(CH₃)—, —CH=CH—, —CH=CH—CH₂—, —CH₂—O—CH₂— and —CH₂—CH₂—O—CH₂—;

each of $R_1$ and $R_2$ independently is hydrogen, $C_1$-$C_4$ alkyl, $C_1$-$C_4$ alkoxy, $C_1$-$C_4$ alkylthio, $C_1$-$C_4$ alkylsulfonyl, halogen or trihalomethyl;

each of $R_3$ and $R_5$, independently, is hydrogen or $C_1$-$C_4$ alkyl;

$R_4$ is a —$OR_6$ or —$N(R_6R_7)$ group, wherein each of $R_6$ and $R_7$ independently is hydrogen, $C_1$-$C_4$ alkyl, phenyl or benzyl; or pharmaceutically acceptable salts thereof.

2. A compound of formula (I), according to claim 1, wherein:

p is 1 or 2;
A is —CH₂— or —CH₂—CH₂—;
$Z_1$ is direct linkage or —CH₂—;
Q is —CH₂—CH₂—, —CH₂—CH₂—CH₂—, CH₂—C(CH₃)₂—, —CH₂—CH₂—C(CH₃)₂—, —CH₂—O—CH₂—, —CH₂—CH₂—O—CH₂—;

each of $R_1$, $R_2$, independently is hydrogen, $C_1$-$C_4$ alkyl, halogen or trifluoromethyl;
$R_3$ is $C_1$-$C_4$ alkyl;
$R_5$ is hydrogen;
$R_4$ is —$OR_6$ or —$NHR_6$ wherein $R_6$ is hydrogen or $C_1$-$C_4$ alkyl or
the pharmaceutically acceptable salts thereof.

3. A compound of formula (I), according to claim 1, wherein:

p is 1 or 2;
A is —CH₂—;
$Z_1$ is a direct linkage or —CH₂—;
Q is —CH₂—CH₂—, —CH₂—CH₂—CH₂—, —CH₂—C(CH₃)₂—; —CH=CH— or —CH₂—O—CH₂—;

$R_2$ and $R_5$ are hydrogen;
$R_3$ is $C_1$-$C_4$ alkyl;
$R_1$ is halogen or trifluoromethyl;
$R_4$ is $OR_6$ or $NHR_6$ wherein $R_6$ is hydrogen or $C_1$-$C_4$ alkyl; or
the pharmaceutically acceptable salts thereof.

4. A compound selected from the group consisting of:

5-Fluoro-1-[[4-(1H-imidazol-1-yl)phenyl]methyl]-3-methyl-1H-indole-2-propanoic acid;

5,7-Difluoro-1-[[4-(1H-imidazol-1-yl)phenyl]methyl]-3-methyl-1H-indole-2-propanoic acid;

5-Fluoro-1-[[3-(1H-imidazol-1-yl)phenyl]methyl]-3-methyl-1H-indole-2-propanoic acid;

5-Fluoro-1-[[4-(1H-imidazol-1-ylmethyl)phenyl]methyl]-3-methyl-1H-indole-2-propanoic acid;

Ethyl 5-fluoro-1-[[4-(1H-imidazol-1-yl)phenyl]methyl]-3-methyl-1H-indole-2-propanoate;

5-Fluoro-1-[[4-(1H-imidazol-1-yl)phenyl]methyl]-3-methyl-1H-indole-2-propanamide;

5-Fluoro-1-[[4-(1H-imidazol-1-yl)phenyl]methyl]-α,α,3-trimethyl-1H-indole-2-propanoic acid;

5,7-Difluoro-1-[[4-(1H-imidazol-1-yl)phenyl]methyl]-α,α,3-trimethyl-1H-indole-2-propanoic acid;

5-Fluoro-1-[[4-(1H-imidazol-1-yl)phenyl]methyl]-3-methyl-1H-indole-2-butanoic acid;

Ethyl 5-fluoro-1-[[4-(1H-imidazol-1-yl)phenyl]methyl]-3-methyl-1H-indole-2-butanoate;

5-Fluoro-1-[[4-(1H-imidazol-1-yl)phenyl]methyl]-α,α,3-trimethyl-1H-indole-2-butanoic acid;

5,7-Difluoro-1-[[4-(1H-imidazol-1-yl)phenyl]methyl]-α,α,3-trimethyl-1H-indole-2-butanoic acid;

or pharmaceutically acceptable salts thereof.

5. A pharmaceutical composition for treating a disease state in which an enhancement of $TXA_2$ synthesis exerts a pathogenic effect, comprising a suitable carrier or diluent or both and, as active principal, an effective amount of a compound of formula I as claimed in claim 1 or a pharmaceutically acceptable salt thereof.

* * * * *

UNITED STATES PATENT AND TRADEMARK OFFICE
CERTIFICATE OF CORRECTION

PATENT NO. : 5,246,957
DATED : SEPTEMBER 21, 1993
INVENTOR(S) : PAOLO COZZI, et al

It is certified that error appears in the above-indentified patent and that said Letters Patent is hereby corrected as shown below:

Column 15, Claim 2, line 21, "$Z_1$" should read -- Z --.

Column 15, Claim 3, line 36, "$Z_1$" should read -- Z --.

Signed and Sealed this

Second Day of August, 1994

*Attest:*

BRUCE LEHMAN

*Attesting Officer*     *Commissioner of Patents and Trademarks*